United States Patent [19]
Parry et al.

[11] 3,997,537
[45] Dec. 14, 1976

[54] PROCESS OF PREPARING 2-AMINO-4-HYDROXY-5(AND/OR 6)-ALKYL SUBSTITUTED PYRIMIDINES

[75] Inventors: David Rees Parry, Wokingham; Alfred Glyn Williams, Basingstoke, both of England

[73] Assignee: Imperial Chemical Industries Limited, London, England

[22] Filed: May 12, 1975

[21] Appl. No.: 576,572

[30] Foreign Application Priority Data

May 20, 1974 United Kingdom ............ 22423/74

[52] U.S. Cl. .................. 260/256.4 C; 260/256.4 E
[51] Int. Cl.² ....................................... C07D 239/36
[58] Field of Search ............. 260/256.4 C, 256.4 E

[56] References Cited
FOREIGN PATENTS OR APPLICATIONS 6,704,665  10/1967  Netherlands ................ 260/256.4 E
1,203,026  8/1970   United Kingdom ........ 260/256 4 E

OTHER PUBLICATIONS

Iwakura, et al., "Chemical Abstracts", vol. 50, 1956, Col. 1028i–1029a.
Baranyovits, et al., "Chemical Abstracts", vol. 71, 1969, Col. 13137r.
Snell, et al., "Chemical Abstracts," vol. 71. 1969, Col. 91517d.

Primary Examiner—Donald G. Daus
Assistant Examiner—James H. Turnipseed
Attorney, Agent, or Firm—Cushman, Darby & Cushman

[57] ABSTRACT

Process for the preparation of a compound of formula:

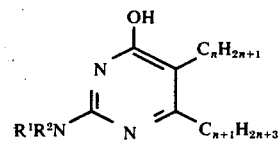

wherein n is zero or an integer from 1 to 12 and $R^1$ and $R^2$ are hydrogen or lower alkyl, which comprises the step of treating a mixture of a diketene of formula:

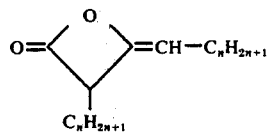

and a strongly acidic medium selected from the group consisting of concentrated sulphuric acid and oleum with a compound of formula:

$$NH=C(NH_2)NR^1R^2$$

or the sulphate thereof.

5 Claims, 1 Drawing Figure

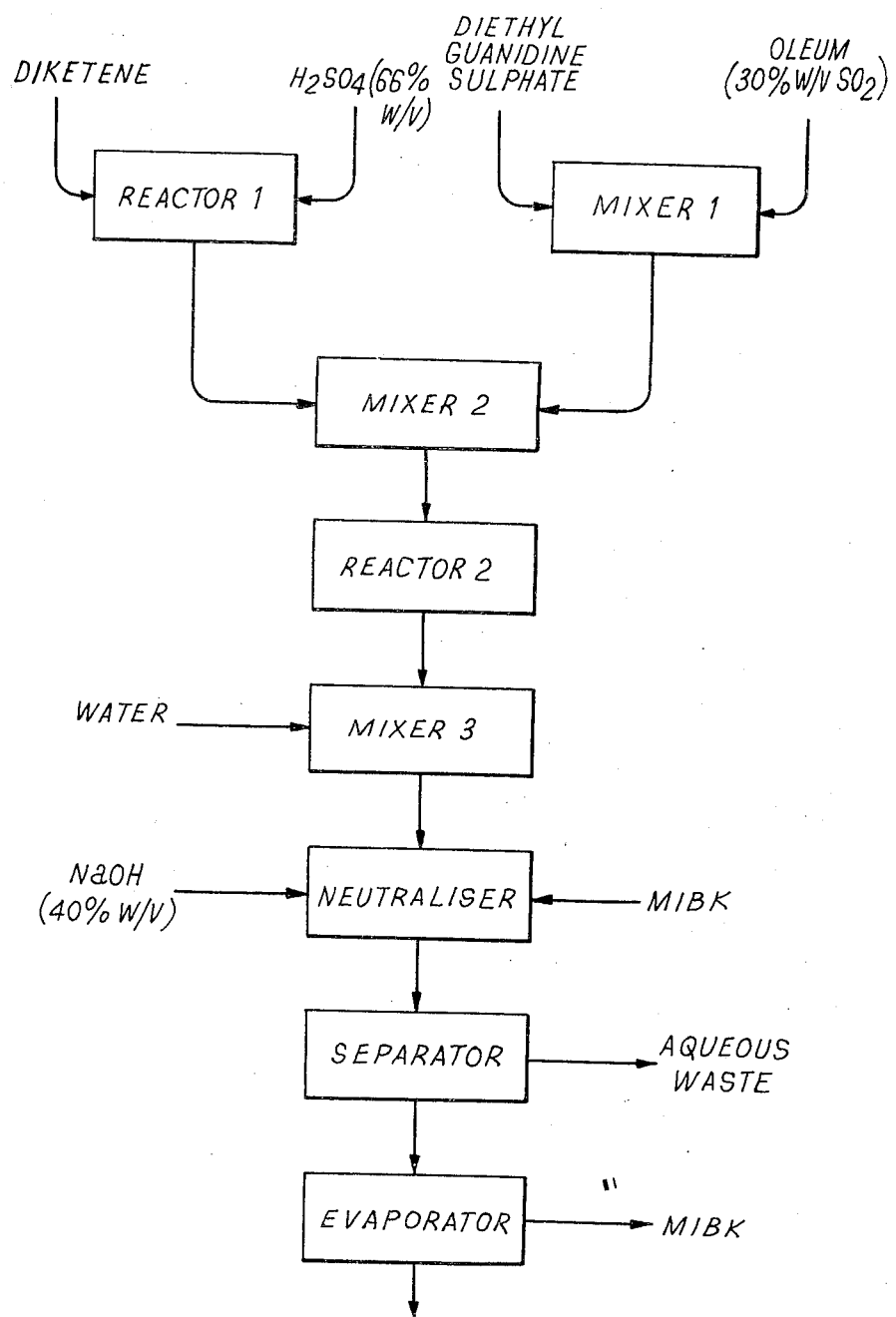

PROCESS OF PREPARING 2-AMINO-4-HYDROXY-5(AND/OR 6)-ALKYL SUBSTITUTED PYRIMIDINES

This invention relates to a process for the preparation of hydroxypyrimidines useful as intermediates in the preparation of pesticides.

4-Hydroxypyrimidines bearing an amino group at the 2-position are intermediates for the preparation of various fungicidal and insecticidal products, including for example, the insecticides pirimiphos-methyl and pirimiphos-ethyl. They have been made by the condensation of an acetoacetic ester with a guanidine under basic conditions. Since acetoacetic esters may be prepared from diketene it was thought that synthesis of 4-hydroxy-pyrimidines from diketene itself would be possible. Various attempts to do this have been reported in the literature. Thus Lacey (J. Chem. Soc., 1954, 839–44) reacted diketene with guanidine carbonate in alkaline solution at the ambient temperature and obtained 2-amino-4-hydroxy-6-methylpyrimidine in 14% yield. Using the guanidine hydrochloride the yield was increased to 28%. However when methylguanidine hydrochloride was used the yield of product was only 8%, and investigation showed that the product was 1,6-dihydro-1,4-dimethyl-2-amino-pyrimidine-6-one and not a hydroxypyrimidine. Similarly Iwakura et al (J. Chem. Soc. Japan, Ind. Chem. Sect., 1954, 57, 947) found that 2-amino-4-hydroxy-6-methylpyrimidine was only obtained in 4% yield when diketene was reacted with guanidine nitrate in the presence of aqueous potassium hydroxide. We have now discovered that substantially higher yields of 2-amino-4-hydroxy-6-alkyl pyrimidines may be obtained by carrying out the reaction of a diketene with a guanidine in strongly acidic media. Furthermore the rate of reaction is sufficiently fast for the process to be operated in a continuous manner.

According to the present invention therefore a process for the preparation of a compound of formula:-

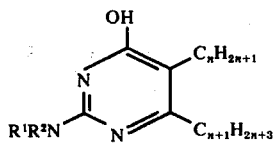

wherein $n$ is zero or an integer from one to twelve, and $R^1$ and $R^2$ are hydrogen or lower alkyl, comprises treating a mixture of a diketene of formula:-

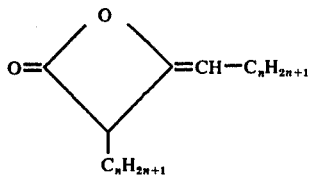

and a strongly acidic medium with a guanidine of formula:-

or an acid addition salt thereof.

The process is particularly useful for the preparation of compounds of the above formula where $n$ is zero.

A preferred strongly acidic medium is concentrated sulphuric acid comprising at least 50% by weight of sulphuric acid, or oleum comprising up to 30% by weight or sulphur trioxide. When an acid-addition salt of the guanidine is used it is preferably the sulphate.

The process is particularly useful for the preparation of 2-dimethylamino-4-hydroxy-6-methyl-pyrimidine and 2-diethylamino-4-hydroxy-6-methyl-pyrimidine.

The diketene may be generated by the dehydrohalogenation of carboxylic acid halides having an α-hydrogen atom under conditions which cause the ketene initially formed to dimerise. The dehydrohalogenation step may be carried out using an organic base such as a trialkylamine (for example, triethylamine) or an aniline (for example diethylaniline) and the ketene thus generated may be caused to dimerise by heating a solution thereof in an inert solvent such as, for example, carbon tetrachloride.

The invention process is illustrated by the following examples.

EXAMPLE 1

This example illustrates the preparation of 2-diethylamino-4-hydroxy-6-methylpyrimidine by a continuous process, with the aid of the accompanying drawing which represents a flow diagram of the process. Diketene and 66% w/v sulphuric acid are separately charged into reactor 1 at a rate of 0.275 M of diketene to every 37.5 ml. of the acid, the reactor temperature being maintained below 20° C, and the mixture discharged into mixer 2. N,N-Diethyl-guanidine sulphate and oleum (30% w/v) are separately charged into mixer 1 (in the ratio of 0.25 M guanidine to 128 ml. oleum) keeping the mixer temperature below 30° C, and the resultant mixture discharged into mixer 2 at a rate equivalent to the discharge of 1.0 M of the guanidine to every 1.1 M of diketene. The total mixture then passes through reactor 2 where the mixture is heated at the reflux temperature of n-propanol (i.e. 95° C) the mixture residence time in the reactor being approximately 10 minutes. After passing through reactor 2 the mixture is diluted with water in mixer 3, and then neutralised with aqueous sodium hydroxide (40% w/v) in the neutraliser. Methyl isobutyl ketone is passed into the neutraliser at the same time as the sodium hydroxide and the product passes into solution in the ketone as the neutralisation proceeds. The mixture then passes into a separator where the aqueous waste liquors are discharged and the ketone phase passes to an evaporator where the solvent is driven off leaving the product, 2-diethylamino-4-hydroxy-6-methylpyrimidine, in about 80% yield based on the guanidine, melting point 131°–132° C. The melting point of a sample purified further by recrystallisation from ethanol was 134°–135° C, but the purity of the product is sufficient for further processing without recrystallisation.

In variations on the above process the sodium hydroxide may be replaced by ammonium hydroxide and the methyl isobutyl ketone by other solvents, such as chloroform.

The heat generated in the dilution step in mixer 3 and the neutraliser may be employed to heat reactor 2.

The solution of product in methyl isobutyl ketone may be employed directly in the process of phosphorylation of the hydroxy pyrimidine without the necessity of evaporation.

EXAMPLE 2

This example illustrates the preparation of 5-n-butyl-2-diethylamino-4-hydroxy-6-n-pentylpyrimidine. (a) Preparation of 3-n-butyl-2-oxo-4-n-pentylidenyloxetane. Triethylamine (26.0 g) was slowly added to a ice-cooled solution of n-hexanoyl chloride (29.6 g) in carbon tetrachloride (75 ml) with stirring. As the addition proceded a white precipitate was formed. When the addition was complete the mixture was stirred at the ambient temperature for 30 minutes and then at 50° C for 90 minutes under an efficient condenser. After cooling to 10° C the mixture was filtered and the solvent evaporated from the filtrate to yield 3-n-butyl-2-oxo-4-n-pentylidenyloxetane (21.2 g) as a pale yellow oil. (b) Preparation of 5-n-butyl-2-diethylamino-4-hydroxy-6-n-pentylpyrimidine.

To a cooled mixture of concentrated sulphuric acid (98% w/v; 10 ml), water (5 ml) and 3-n-butyl-2-oxo-n-4-pentylidenyloxetane(21.2 g) was added, in small portions with external cooling of the mixture, diethylguanidine sulphate (16.4 g), followed by oleum (20% w/v, 50 ml). The resultant mixture was heated to 60° C for 30 minutes, after which the resultant dark brown solution was cooled, diluted with water and neutralised with ammonia solution (s.g. = 0.880). The oily precipitate crystallised on standing and was collected by filtration, and recrystallised from ethanol to yield 5-n-butyl-2-diethylamino-4-hydroxy-6-n-pentyl pentylpyrimidine, melting point 77° C.

EXAMPLE 3

By procedures similar to those illustrated in Example 2 the following pyrimidines were prepared from the corresponding diketenes, which themselves were obtained from the acid chlorides.

2-diethylamino-4-hydroxy-6-methylpyrimidine (m.p. 131°–132° C), 2-diethylamino-5-ethyl-4-hydroxy-6-n-propylpyrimidine (m.p. 88°–89° C), 6-n-butyl-2-diethylamino-4-hydroxy-5-n-propylpyrimidine (m.p. 93°–94° C), 2-diethylamino-4-hydroxy-6-n-hexyl-5-n-pentylpyrimidine (m.p. 72° C), 2-diethylamino-4-hydroxy-6-n-heptyl-5-n-hexylpyrimidine. (m.p. 70° C), 2-diethylamino-5-n-heptyl-4-hydroxy-6-n-octylpyrimidine (m.p. 110°–111° C)

2-diethylamino-4-hydroxy-6-n-nonyl-5-n-octylpyrimidine (m.p. 40° C)

5-n-decyl-2-diethylamino-4-hydroxy-6-n-undecylpyrimidine (m.p. 40°–41° C).

We claim:

1. Process for the preparation of a compound of formula:-

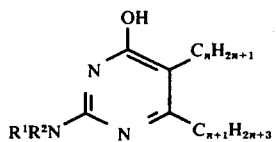

wherein $n$ is zero or an integer from 1 to 12 and $R^1$ and $R^2$ are hydrogen or lower alkyl, which comprises the step of treating a mixture of a diketene of formula:-

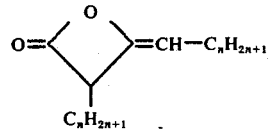

and a strongly acidic medium selected from the group consisting of concentrated sulphuric acid and oleum with a compound of formula:-

$$NH=C(NH_2)NR^1R^2$$

or the sulphate thereof.

2. Process as claimed in claim 1 wherein $n$ is zero.

3. Process as claimed in claim 1 wherein the strongly acidic medium is concentrated sulphuric acid comprising at least 50% by weight of sulphuric acid.

4. Process as claimed in claim 1 wherein the strongly acidic medium is oleum comprising up to 30% by weight of sulphur trioxide.

5. Process as claimed in claim 1 where the compound of formula:-

$$NH=C(NH_2)NR^1R^2$$

is used in the form of the sulphate salt.

* * * * *